(12) United States Patent
Veau et al.

(10) Patent No.: US 8,672,537 B2
(45) Date of Patent: Mar. 18, 2014

(54) METHOD AND DEVICE FOR THE DETECTION AND/OR MEASUREMENT OF FOULING IN HEAT EXCHANGERS

(75) Inventors: José Veau, Montesson (FR); Marc Petit, Pontoise (FR); Patrice Tochon, Uriage (FR); Patrice Clement, Saint Egreve (FR)

(73) Assignees: Electricite de France, Paris (FR); Commissariat a l'Energie Atomique, Paris (FR)

( * ) Notice: Subject to any disclaimer, the term of this patent is extended or adjusted under 35 U.S.C. 154(b) by 575 days.

(21) Appl. No.: 12/999,622

(22) PCT Filed: Jun. 18, 2009

(86) PCT No.: PCT/EP2009/057629
§ 371 (c)(1),
(2), (4) Date: Dec. 16, 2010

(87) PCT Pub. No.: WO2009/153323
PCT Pub. Date: Dec. 23, 2009

(65) Prior Publication Data
US 2011/0080182 A1 Apr. 7, 2011

(30) Foreign Application Priority Data

Jun. 18, 2008 (FR) ...................................... 08 54030

(51) Int. Cl.
*G01N 25/00* (2006.01)
*G01N 17/00* (2006.01)
*G01K 13/00* (2006.01)
*G01K 7/00* (2006.01)

(52) U.S. Cl.
USPC .................................... 374/7; 57/147; 57/183

(58) Field of Classification Search
USPC ....................................... 374/7, 57, 147, 183
See application file for complete search history.

(56) References Cited

U.S. PATENT DOCUMENTS

| 3,721,897 A | 3/1973 | Edling |
| 3,810,009 A * | 5/1974 | Hausler et al. .................... 374/7 |

(Continued)

FOREIGN PATENT DOCUMENTS

| FR | 2 897 930 | 8/2007 |
| WO | WO 01/94876 A1 | 12/2001 |

*Primary Examiner* — Mirellys Jagan
(74) *Attorney, Agent, or Firm* — Blakely Sokoloff Taylor & Zafman

(57) ABSTRACT

The invention relates to a method for the detection and/or measurement of fouling in a heat exchanger, whereby the resistance value ($R_1$, $R_2$) of a resistor (R), placed on a wall (P) of this heat exchanger, is measured at two different instants and a value of the measurements ($R_2$; $R_1$) that corresponds to a function of the values measured at these two instants is determined, characterized in that the resistor (R) is subjected in succession to two power levels ($P_1$, $P_2$) that are each maintained for a certain duration, the first power level ($P_1$) being below the second power level ($P_2$), and the measurements of the two resistance values ($R_1$, $R_2$) being respectively carried out during application of these two power levels. The invention also relates to a device for the detection and/or measurement of fouling in a heat exchanger, characterized in that it includes a resistor (R), placed on a wall (P) of this heat exchanger, means (16) for delivering a constant power to said resistor (R) and processing means (17), these various means being capable of implementing the method according to the invention Finally, the invention relates to the use of said method or of said device.

12 Claims, 3 Drawing Sheets

(56) References Cited

U.S. PATENT DOCUMENTS

| | | | |
|---|---|---|---|
| 3,913,378 A * | 10/1975 | Hausler | 374/7 |
| 4,722,610 A * | 2/1988 | Levert et al. | 374/43 |
| 5,248,198 A * | 9/1993 | Droege | 374/7 |
| 5,429,178 A * | 7/1995 | Garey et al. | 165/11.1 |
| 6,288,528 B1 * | 9/2001 | Goodstine et al. | 324/71.1 |
| 6,386,272 B1 * | 5/2002 | Starner et al. | 165/11.1 |
| 2003/0048830 A1 * | 3/2003 | Dickerman et al. | 374/103 |
| 2005/0105583 A1 * | 5/2005 | Xiao et al. | 374/29 |
| 2009/0000764 A1 * | 1/2009 | Tochon et al. | 165/11.1 |

\* cited by examiner

METHOD AND DEVICE FOR THE DETECTION AND/OR MEASUREMENT OF FOULING IN HEAT EXCHANGERS

GENERAL TECHNICAL FIELD AND PRIOR ART

The present invention pertains to the detection and/or to the measurement of fouling in heat exchangers.

The problem of fouling in heat exchangers is an issue of increasing importance in industry. Numerous studies have been conducted to reduce this fouling, but at the present time none has led to any significant gain.

Two large classes of industrial applications particularly represent major challenges.

The first is the agri-foodstuff industry in which the reducing or better controlling of fouling represents savings in operating time and hence gains in productivity. For example, a 2-hour reduction between two cleaning cycles corresponds to a minimum productivity gain of 10%. In addition, a decrease in fouling leads to a decrease in consumption of detergents and other maintenance products. Finally, better control over fouling implies better process control and hence superior product quality.

The second class of applications is industrial cooling, notably for the chemical, petro-chemical industries and in energy production (thermal and nuclear plants). The power rating of these systems is effectively very high, which means that lowered performance has a direct impact on production yields. Also, fouling necessarily generates a drop in heat exchange capacity and therefore creates a potential risk of overheating in these systems. This is the case in particular for the cooling of nuclear plants in periods of excessively hot weather.

These two examples of application classes are evidently not limiting, the detection and/or measurement of fouling obviously being possibly essential in other industries.

The invention therefore applies to all types of industries.

The general objective is to propose a solution for detecting and/or measuring fouling in exchangers of any type.

Numerous techniques are already known, intended to allow the detection of possible fouling in a heat exchanger.

Most existing devices are based on parietal heat flux measurement and on observation of the variation in the temporal value thereof, which can be correlated to a greater or lesser extent with fouling occurring at the measuring probe.

Active probes have been developed for example, which jointly use electric resistance and temperature measurement to determine the variation in coefficient of local heat exchange, placed over the naturally conveyed flow.

Application WO 01 94 876 notably proposes a method for monitoring the fouling of the heat exchanger in a combustion vessel.

According to the method described in this patent application, a resistance value is evaluated of a network which may be formed by the wall tubes of a heat exchanger. For this purpose, the network is subjected to one or more given electric signals. The resistance value thus calculated is itself compared with a nominal resistance value determined on the same circuit at a prior reference time. The resistance value obtained is compared for example with a threshold value, on and after which it is considered that there is fouling.

The solution put forward in this application WO 01 94 876 has the drawback however that it can only be used when the reactor is operating at a given flow rate and temperature, and in particular at the flow rate and operating temperature of the reactor when the value of the reference resistance was measured.

On account of this shortcoming, this solution is relatively unsuitable for a good number of applications.

GENERAL DISCLOSURE OF THE INVENTION

One objective of the invention is to propose a solution for detecting and/or measuring fouling in a heat exchanger which can be implemented independently of variations in conditions, notably of flow rate and temperature conditions, to which the exchanger is subjected.

A further objective is to propose a solution for detecting and/or measuring fouling that is simple and non-intrusive.

For this purpose, the invention proposes a method for detecting and/or measuring fouling in a heat exchanger in which the resistance value of a resistor arranged on a wall of this exchanger is measured at two different instants, and a measurement value is determined corresponding to a function of the measured resistance values measured at these two instants, characterized in that the resistor is subjected in succession to two power levels that are each maintained for a certain duration, the first power level being lower than the second, the measurements of the two resistance values respectively being taken at the time these two power levels are applied.

In particular, the first power level can be chosen, for the period of application thereof, so that the heat flow caused by the Joule effect has an influence on the exchanger surface and not on the fouling layer if any exists.

The second power level can be chosen so that the heat flow caused by the Joule effect has an impact both on the exchanger and on the fouling deposit if there is any such deposit.

The invention also proposes a device for the detection and/or measurement of fouling in a heat exchanger, characterized in that it comprises a resistor arranged on a wall of this exchanger, means to supply said resistor R with constant power, and processing means, these different means being capable of implementing the above-cited method.

Finally, the invention also relates to the use of this method or of this device for the detection and/or measurement of fouling in the agri-foodstuff industry or in industrial thermal applications.

DESCRIPTION OF THE FIGURES

Other characteristics and advantages of the invention will become further apparent from the following description which is solely illustrative and is non-limiting, and is to be read in connection with the appended figures in which.

DESCRIPTION OF ONE OR MORE EMBODIMENTS AND IMPLEMENTATIONS

Figure 1:
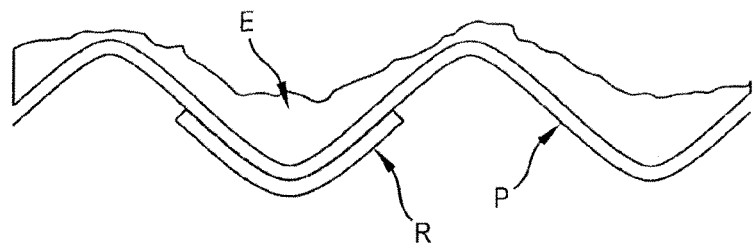
FIG. 1 schematically illustrates a fouled heat exchanger plate equipped with a surface resistor conforming to one possible embodiment of the embodiment.

FIG. 1 shows an exchanger plate P on which fouling deposits E have occurred over time.

This exchanger can be of any type, notably an internal or external convection exchanger, liquid/gas, gas/gas or liquid/liquid.

A surface electric resistor R with positive or negative temperature coefficient is arranged along the exchange wall formed by this plate P. Evidently, the exchanger may not be a plate exchanger, but a tube exchanger, the resistor being arranged along one or more tubes.

Figure 2:
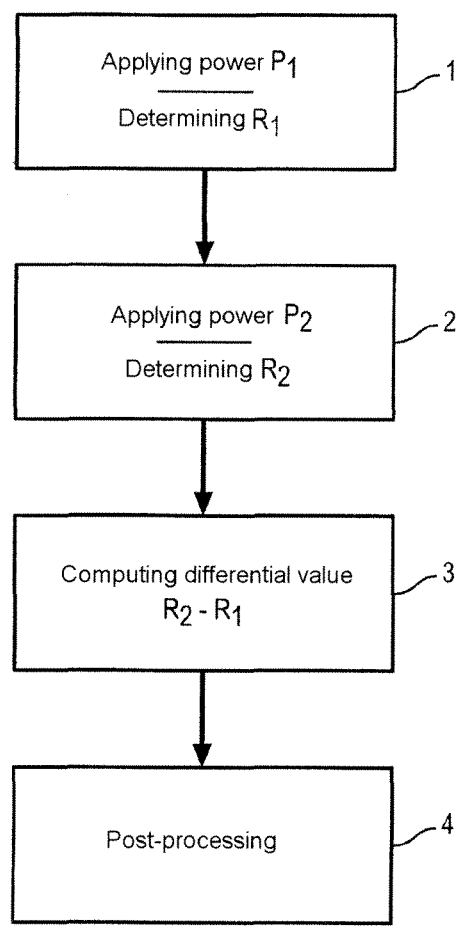
FIG. 2 is a block diagram showing the different steps of a treatment conforming to one embodiment of the invention.

As illustrated in FIG. 2, this surface electric resistor is subjected in succession to two power levels P1 and P2, and the values R1 and R2 are determined of the resistor R when these two levels of power are applied (steps 1 and 2).

Power P1 is chosen at a level which is both sufficient to create significant heating of the resistor R (of the order of a few tenths of a degree) but which at the same time is sufficiently low so that the flow of local heat caused by Joule effect—throughout the time during which this power P1 is applied to the resistor R—only has an impact on the plate P (or tube) of the exchanger and not on the deposit E, the low heat not permitting diffusion as far as the deposit. In practice, at this power level convective phenomena are confined to the wall.

Power P2 is greater and is chosen so that the flow of local heat caused by the Joule effect has an impact both on the plate P (or tube[s]) and on the deposit E if such exists.

Figure 3A:
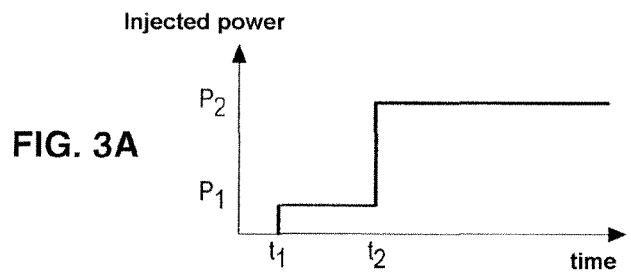
FIGS. 3A to 3C respectively illustrate an example of a time curve of electric power injected into the surface resistor used in the detection device, and time curves of corresponding resistance values for cases in which the plate is not fouled and cases in which it is fouled.

FIG. 3A illustrates the time curve of the power applied to the resistor R, this power being at level P1 between time T1 and time T2, then changes to a higher level P2 on and after time T2.

Power P1 is typically a few tenths of a watt (from 0.1 to 1 watt, typically between 0.2 and 0.8 watt), whilst power P2 is typically of several watts (from 1 to 10 watts, for example between 2 and 6 watts).

The period between time T2 and time T1 during which power P1 is applied is typically a few tens of seconds, power P2 typically being applied for a duration of a few hundred seconds.

These durations and their succession are chosen so as to remain within the same unit of time to ensure the stability of operating conditions and to reach a stabilized heat schedule at the end of the application of powers P1 and P2, the achieving of this stabilized heat schedule being easily within the reach of the person skilled in the art.

Figure 3B:
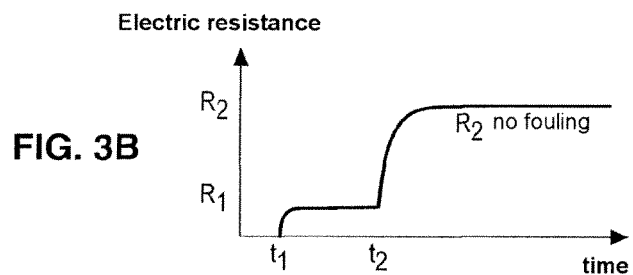
Figure 3C:
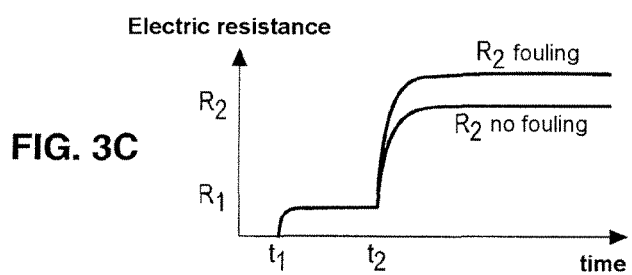

Owing to the low value of power P1 applied so that the flow of heat caused by Joule effect has an influence limited to the plate P alone, the value R1 of the resistor R only depends on operating conditions whether or not the plate P is fouled by a deposit E. On the other hand, during application of the higher P2 level, the value R2 of this resistor R depends both upon operating conditions and on the fact that the plate P is or is not fouled (FIGS. 3B and 3C).

Once the values R1 and R2 of the resistor R have been determined, a function of these two values is determined, typically the subtraction of one from the other (step 3). Since the heat flows transiting through the resistor R are affected by convective heat exchange at the wall and are therefore dependent on the level of fouling of the surface under consideration and on operating conditions, the value of the function of the resistances thus obtained forms a characteristic value of the level of fouling of said surface. In addition, this value has the advantage of being unaffected by conditions surrounding the said surface and notably conditions of variation in flow rate or temperature.

This function value of R1 and R2 thus calculated is then the subject of post-processing (step 4), e.g. for monitoring over the course of time, filtering and comparison with threshold values.

As will have been understood, measurement is non-intrusive with the above-proposed method (since it lies distant from the fouling area and does not perturb fouling dynamics). It is global in that it integrates the entire surface occupied by the resistor. It can adapt to highly diverse geometries and dimensions.

The detection element formed by the sensitive surface element is a metal electric circuit 10 for example, arranged on a dielectric substrate 11 (e.g. polyimide) of narrow thickness imparting certain flexibility and hence facilitated adaptation to almost any type of substrate. This detection element 10 is of free form. It extends over a planar sensitivity area of a few square millimeters or a few square centimeters, the size of this area depending on the size of the sample or of the area to be tested.

Figure 4:
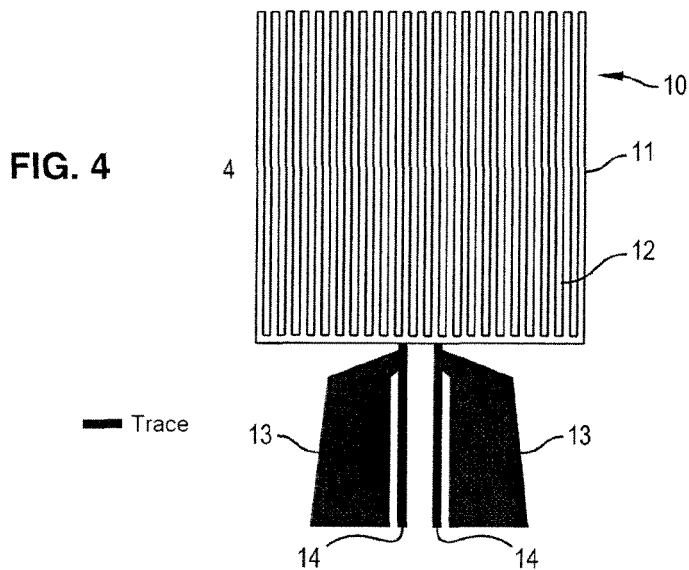
FIG. 4 schematically illustrates an example of a surface resistor which can be used to implement the proposed method.

FIG. 4 gives an example of a possible configuration for this detection element. It comprises a square-shaped patch (side of width L1=40 mm) on which a coiled circuit 12 is deposited and which is supplied by two traces 13 intended to be connected to an outside power supply, two other traces 14—arranged parallel to traces 13—also allowing measurement of the supply voltage to this detection element 10.

Other shapes are evidently possible for this resistor, which may also be rectangular, oval, circular, even of more complex shape.

This resistor must be positioned in thermal contact with the exchanger under consideration, as close as possible to the side on which fouling occurs. The coiled circuit, for example, may be deposited directly on the surface of the exchanger.

The deposited circuit may be in nickel, platinum or copper, or any alloy containing these metals, since all three have the property of having a high temperature coefficient ($K^1$). Other types of metal can be used if they have a good thermoelectric coefficient, i.e. good variation in resistance proportional to the temperature of the circuit.

Figure 5:
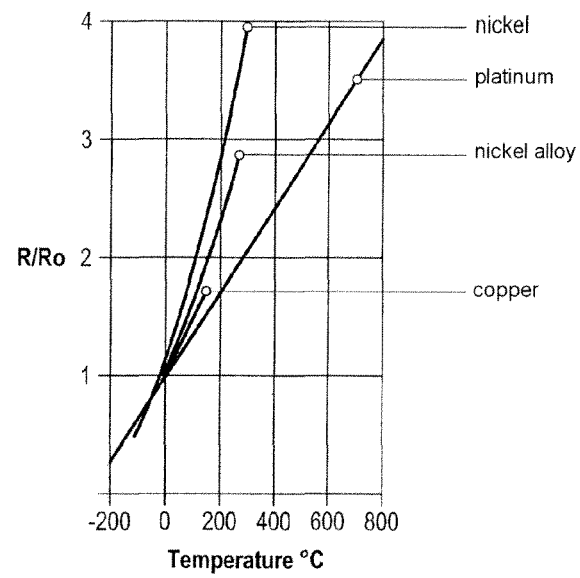
FIG. 5 illustrates different trends in resistance variation as a function of temperature for different possible resistor materials.

Curves of this variation in ohmic resistance as a function of temperature for copper, nickel alloy, pure nickel or platinum are given in FIG. 5.

As a further variant, the resistor R can be directly serigraphied on the final substrate (exchanger wall); the system is even less intrusive and allows high temperature operation.

Figure 6:
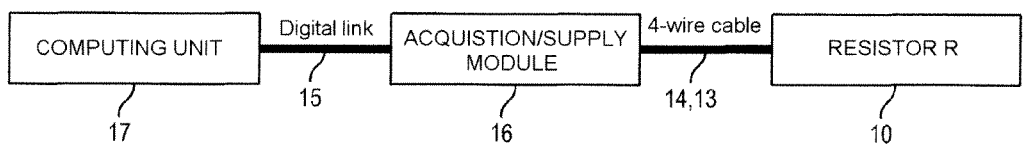
FIG. 6 is a block diagram illustrating an example of a fouling measuring device.

As illustrated in FIG. 6, the detection element formed by the heating surface resistor 10 is electronically connected via a 4-wire cable (wires 13 and 14) to a supply and acquisition module 16.

This electronic module 16 electrically supplies the variable resistance probe 10 by maintaining constant dissipated power in real-time and over time, whether at level P1 or at level P2. For this purpose, it adapts the voltage U at the terminals of the wires in real-time, so that the product of voltage multiplied by intensity remains constant.

A microcomputer 1 is used for this purpose, connected in series with the module 16 e.g. via a USB cable, which permanently analyses the product of voltage by intensity and regulates this product around the initially set point. The set power is variable ranging from very small values (a few tenths of a watt to a few watts). The low power P1 allows measurement of the resistor without producing significant heating thereof (principle of thermistors and others PT100, PT1000).

The high power P2 generates thermal heating entailing a significant change in the ohmic resistance of the probe.

From these two measurements, the computer deduces the value of the function of R2 and R1 which is correlated with the thickness of the deposit.

For this purpose, the electronic module 16 has a digital output allowing transfer of changes in magnitudes of U and I in real time to the computer 17, which determines the value of ohmic resistance (ratio of U to I). As a variant, the computer 17 may be a microcomputer integrated in the electronic module, to perform direct calculation of resistance and differential values.

The characteristics of the electronic module are the following for example:
- maximum voltage 24 Vdc, maximum current 2 Adc;
- Power adjustable from 0.2 W to 10 W in increments of 0.01 W for probes whose resistance varies between 3 and 50 Ohms;
- Measurement of current/voltage with a resolution of 18 bits and accuracy better than 1%;
- 4-wire connection of the resistor;
- Power regulation better than 1%;
- Sampling speed 10 Pts/s.

The computer 17 collects the data in real time in digital file format and performs post-processing on this data to identify fouling status. This processing, for example, may comprise analysis of changes in the differential value of the electric resistor R, which increases as and when the deposit is formed.

Figure 7:
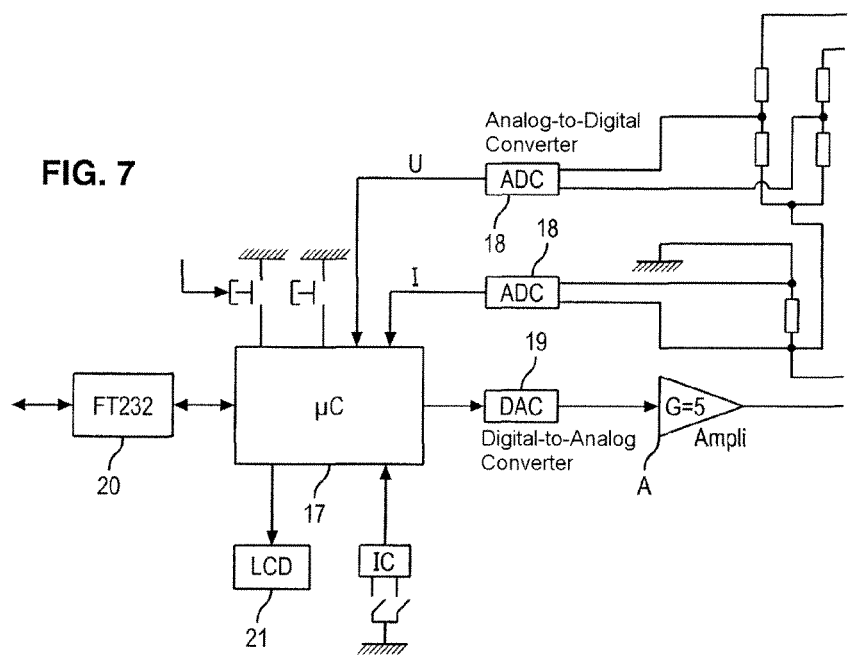
FIG. 7, finally, illustrates an example of the acquisition and supply electronics for said device.

One example of embodiment of the data acquisition and power regulation module integrated in the computer is illustrated in FIG. 7. The computer 17 is a microcomputer which, from two analog/digital converters 18, receives values of voltage U and intensity I measured on the surface resistor R. This computer 17, via a digital/analog converter and an amplifier A, transmits the voltage to be applied to the surface resistor R to maintain the injected power at level P1 or level P2.

It is also connected via a link 20 e.g. of RS232 type, to external processing means (not illustrated). Interface means 21 are optionally provided locally, for example to allow the display of measurements computed by the module.

The technique just described has numerous advantages. It only requires particularly simple electronics which can be made compact and are easily embedded.

It is also of low-cost fabrication.

In addition, it is highly robust and reliable, whilst being easily adapted to any form and any size of heat exchanger.

It further allows global measurement of fouling for the entire instrumented surface within the exchanger, and not point measurement, providing monitoring over time whilst being fully non-intrusive.

The invention claimed is:

1. Method for at least one of detecting and measuring of fouling in a heat exchanger, comprising: measuring a resistance value (R1, R2) of a resistor (R) arranged on a all (P) of the exchanger at two different instants, and determining a value of the measurements as a function of the resistance values measured at the two instants wherein the resistor (R) is arranged along the wall (P) outside the exchanger and the resistor (R) is subjected in succession to first and second power levels (P1, P2) that are each maintained for a certain duration, the duration of application (T1) of the first power level (P1) being smaller than the duration of application (T2) of the second power level (P2), the first power level (P1) being lower than the second power level (P2), and the measuring of the two resistance values (R1, R2) are respectively carried out during application of the two power levels.

2. The method according to claim 1, wherein the voltage (U) applied to the resistor (R) is adapted in real time so that the power (P1, P2) to which this resistor is subjected remains constant for a certain time.

3. The method according to claim 1 wherein the at least one of detecting and measuring of fouling of said heat exchangers is for the agri-foodstuff industry or industrial thermal applications.

4. The method according to claim 1, wherein the first power level (P1) is chosen, for the duration of application thereof, so that the heat flow caused by a Joule effect has an influence on the exchanger wall (P) and not on the layer of fouling (E) if any.

5. The method according to claim 4, wherein the second power level (P2) is chosen so that the heat flow caused by the Joule effect has an impact both on the exchanger wall (P) and on the fouling layer (E) if any.

6. The method according to claim 1, wherein the function of the resistance values is the difference in resistance values measured at two successive instants corresponding to the two power levels.

7. The method according to claim 6, wherein the difference in resistance values (R2−R1) thus obtained is monitored in real time.

8. Device for at least one of detecting and measuring fouling in a heat exchanger, comprising:
   - a resistor (R) arranged on a wall (P) of the exchanger,
   - means (16) to supply said resistor (R) with constant power, and
   - processing means (17), the supply means and processing means configured to implement the method according to claim 1.

9. The device according to claim 8, wherein the at least one of detecting and measuring of fouling in said heat exchanger is in the agri-foodstuff industry or in industrial thermal applications.

10. The device according to claim 8, wherein the resistor (R) is surface resistor.

11. The device according to claim 10, wherein the surface resistor (R) has a dielectric substrate (11) allowing it to adapt to the form of the exchanger.

12. The device according to any of claims 8, 10 or 11, wherein the surface resistor (R) has a coiled resistive circuit (12).

* * * * *

UNITED STATES PATENT AND TRADEMARK OFFICE
CERTIFICATE OF CORRECTION

PATENT NO. : 8,672,537 B2  
APPLICATION NO. : 12/999622  
DATED : March 18, 2014  
INVENTOR(S) : Jose Veau et al.

Page 1 of 1

It is certified that error appears in the above-identified patent and that said Letters Patent is hereby corrected as shown below:

On the Title Page, in Item (73), under Assignees, at line 2, please insert --et aux Energies Alternatives-- after "Atomique".

In the Claims

Column 5, Claim 1, line 55, please delete "all" and insert --wall--.

Signed and Sealed this  
Twenty-first Day of October, 2014

Michelle K. Lee  
*Deputy Director of the United States Patent and Trademark Office*